US 12,403,318 B2

(12) United States Patent
Young et al.

(10) Patent No.: US 12,403,318 B2
(45) Date of Patent: Sep. 2, 2025

(54) CERAMIC ENCLOSURE FOR RECHARGEABLE MEDICAL DEVICES

(71) Applicant: Medtronic, Inc., Minneapolis, MN (US)

(72) Inventors: Paul B. Young, New Richmond, WI (US); Rajesh V. Iyer, Eden Prairie, MN (US); Andrew J. Thom, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 545 days.

(21) Appl. No.: 18/050,361

(22) Filed: Oct. 27, 2022

(65) Prior Publication Data
US 2023/0158313 A1    May 25, 2023

Related U.S. Application Data

(60) Provisional application No. 63/283,064, filed on Nov. 24, 2021.

(51) Int. Cl.
*A61N 1/375* (2006.01)
*A61N 1/378* (2006.01)
*H02J 50/10* (2016.01)

(52) U.S. Cl.
CPC .......... *A61N 1/375* (2013.01); *A61N 1/3787* (2013.01); *H02J 50/10* (2016.02)

(58) Field of Classification Search
CPC .. A61N 1/375; A61N 1/3787; A61N 1/37512; A61N 1/3758; H02J 50/10
See application file for complete search history.

(56) References Cited

U.S. PATENT DOCUMENTS

| 5,117,824 A | 6/1992 | Keimel et al. |
| 5,548,218 A | 8/1996 | Lu |
| 5,782,891 A | 7/1998 | Hassler et al. |
| 6,008,622 A | 12/1999 | Nakawatase |
| 6,185,452 B1 | 2/2001 | Schulman et al. |
| 6,411,854 B1 | 6/2002 | Tziviskos et al. |
| 6,459,924 B1 | 10/2002 | Creighton, IV |

(Continued)

FOREIGN PATENT DOCUMENTS

| EP | 0693733 A1 | 1/1996 |
| EP | 3045203 A2 | 7/2016 |

(Continued)

OTHER PUBLICATIONS

De Troye et al., "The Calculation and Measurement of Helmholtz Coil Fields," Army Research Laboratory, Nov. 1994, 20 pp.

(Continued)

*Primary Examiner* — Eugene T Wu
(74) *Attorney, Agent, or Firm* — Shumaker & Sieffert, P.A.

(57) ABSTRACT

In some examples a medical device includes circuitry configured to at least one of sense a physiological parameter of a patient or deliver a therapy to the patient. The medical device may also include a housing configured to house the circuitry, wherein the housing includes a plurality of structural members and an attachment mechanism that joins the plurality of structural members. The attachment mechanism may be configured to suppress induced currents in the housing when the medical device is exposed to a time-varying magnetic field.

20 Claims, 6 Drawing Sheets

(56) References Cited

U.S. PATENT DOCUMENTS

| | | | |
|---|---|---|---|
| 7,474,098 B2 | 1/2009 | King | |
| 7,816,915 B2 | 10/2010 | Susel et al. | |
| 7,924,000 B2 | 4/2011 | Susel et al. | |
| 8,175,716 B2 | 5/2012 | Rahman et al. | |
| 8,401,648 B2 * | 3/2013 | Kast | A61N 1/375 607/36 |
| 8,612,014 B2 | 12/2013 | Rahman et al. | |
| 8,634,928 B1 | 1/2014 | O'Driscoll et al. | |
| 9,259,591 B2 | 2/2016 | Brown et al. | |
| 9,318,780 B2 | 4/2016 | Robertson et al. | |
| 9,620,985 B2 | 4/2017 | Rosenfeld | |
| 9,711,272 B2 | 7/2017 | Hassan-Ali et al. | |
| 10,355,512 B2 | 7/2019 | Cinbis et al. | |
| 10,821,292 B2 | 11/2020 | Iyer et al. | |
| 2002/0177884 A1 | 11/2002 | Ahn et al. | |
| 2004/0135579 A1 | 7/2004 | Takizawa et al. | |
| 2008/0027513 A1 | 1/2008 | Carbunaru et al. | |
| 2008/0243218 A1 * | 10/2008 | Bottomley | A61N 1/086 324/318 |
| 2010/0114275 A1 * | 5/2010 | Min | A61N 1/05 607/116 |
| 2010/0201315 A1 | 8/2010 | Oshimi et al. | |
| 2011/0257703 A1 | 10/2011 | Kerber et al. | |
| 2011/0295340 A1 | 12/2011 | Rahman | |
| 2011/0301668 A1 | 12/2011 | Forsell | |
| 2012/0248883 A1 | 10/2012 | Konanur et al. | |
| 2013/0024059 A1 | 1/2013 | Miller et al. | |
| 2013/0043734 A1 | 2/2013 | Stone | |
| 2013/0223028 A1 | 8/2013 | Ame et al. | |
| 2013/0241300 A1 | 9/2013 | Miyamoto | |
| 2013/0241302 A1 | 9/2013 | Miyamoto et al. | |
| 2013/0285466 A1 | 10/2013 | Wissenwasser et al. | |
| 2014/0028109 A1 | 1/2014 | Simon et al. | |
| 2014/0094674 A1 | 4/2014 | Nurmikko et al. | |
| 2014/0243848 A1 | 8/2014 | Auricchio et al. | |
| 2014/0265620 A1 | 9/2014 | Hoarau et al. | |
| 2014/0346886 A1 | 11/2014 | Yang et al. | |
| 2015/0018917 A1 * | 1/2015 | Wechter | A61N 1/05 607/116 |
| 2015/0321012 A1 | 11/2015 | Cinbis et al. | |
| 2016/0022142 A1 | 1/2016 | Bradshaw | |
| 2016/0111208 A1 | 4/2016 | Park | |
| 2016/0111913 A1 | 4/2016 | Robertson et al. | |
| 2016/0131725 A1 | 5/2016 | Sambrandamurthy et al. | |
| 2016/0141097 A1 | 5/2016 | Oo et al. | |
| 2016/0189848 A1 | 6/2016 | Nam | |
| 2017/0001003 A1 | 1/2017 | Pivonka et al. | |
| 2017/0025888 A1 | 1/2017 | Cinbis et al. | |
| 2017/0047636 A1 | 2/2017 | Lee et al. | |
| 2017/0202467 A1 | 7/2017 | Zitnik et al. | |
| 2017/0203109 A1 | 7/2017 | Maile et al. | |
| 2017/0281955 A1 | 10/2017 | Maile et al. | |
| 2018/0140850 A1 | 5/2018 | Linder et al. | |
| 2018/0140851 A1 | 5/2018 | Maile et al. | |
| 2018/0140852 A1 | 5/2018 | Linder et al. | |
| 2018/0140853 A1 | 5/2018 | Maile et al. | |
| 2018/0141444 A1 | 5/2018 | Lee et al. | |
| 2019/0199132 A1 | 6/2019 | Ota et al. | |
| 2019/0275328 A1 | 9/2019 | Zitnik et al. | |
| 2020/0001094 A1 | 1/2020 | Iyer et al. | |
| 2020/0260991 A1 | 8/2020 | Rowland et al. | |
| 2020/0384260 A1 | 12/2020 | Tischendorf et al. | |
| 2021/0001130 A1 | 1/2021 | Wolf, II | |
| 2021/0001131 A1 | 1/2021 | Iyer et al. | |

FOREIGN PATENT DOCUMENTS

| | | |
|---|---|---|
| WO | 2000056394 A1 | 9/2000 |
| WO | 0197908 A2 | 12/2001 |
| WO | 2018102435 A1 | 6/2018 |
| WO | 2020251900 A1 | 12/2020 |

OTHER PUBLICATIONS

Jia et al., "The optimization of wireless power transmission: design and realization," The International Journal of Medical Robotics and Computer Assisted Surgery, Feb. 2012, pp. 337-347.

Lenaerts et al., "Inductive powering of a freely moving system," Sensors and Actuators, A 123-124, Jan. 2005, pp. 522-530.

Maile PHD, et al., "Wireless Power Transfer for Deeply Implanted Medical Devices (IMD)," Boston Scientific, presented Dec. 5-7, 2016 at Biological & Chemical Sensors Summit, San Diego, CA, 20 slides.

Tang et al., "A Low-Operating-Voltage Wireless Intermediate-Range Scheme for Energy and Signal Transmission by Magnet Coupling for Implantable Devices," IEEE Journal of Emerging and Selected Topics in Power Electronics, vol. 3, No. 1, Mar. 2015, pp. 242-251.

Von Novak, "Power Systems for Medical Implants," Qualcomm Technologies, Inc., presented Dec. 5-7, 2016 at Biological & Chemical Sensors Summit, San Diego, CA, 24 slides.

Wilken-Resman, et al., "Power Transfer Prediction Tool for Medical Implants," Qualcomm Technologies, presented Dec. 5-7, 2016 at Biological & Chemical Sensors Summit, San Diego, CA, 15 slides.

Yates, "Wireless power delivery for ventricular assist devices," Imperial College, London, Dec. 7, 2017, presented Dec. 5-7, 2017 at Biological & Chemical Sensors Summit, San Diego, CA, 40 slides.

* cited by examiner

CERAMIC ENCLOSURE FOR RECHARGEABLE MEDICAL DEVICES

This application claims the benefit of U.S. Provisional Application Ser. No. 63/283,064, filed Nov. 24, 2021, which is entitled "CERAMIC ENCLOSURE FOR RECHARGEABLE MEDICAL DEVICES" and is incorporated by reference herein in its entirety.

TECHNICAL FIELD

The disclosure relates generally to implantable medical devices (IMDs) and, more particularly, rechargeable IMDs.

BACKGROUND

Various IMDs have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device housing. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, or transvenously. By way of illustrative example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart with or without the need for external leads, have been proposed, built, and adapted to provide both pacing and other electrical therapy to the patient.

SUMMARY

The disclosure describes IMDs, systems, and associated techniques, structures, and assemblies configured to suppress induced currents in the housing of IMDs when the IMDs are subject to time-varying magnetic fields, particularly for recharging a rechargeable power source of the IMDs.

The size of recharge coils in IMDs get smaller as the IMDs themselves get smaller. Smaller IMDs with small recharge coils may require charging signals at higher frequencies. Also, to reduce recharge burden on patients, there is a desire to reduce charging session duration, which may be achieved by charging signals at higher frequencies and/or magnitudes. Ceramic enclosures may be used to replace conventional titanium (Ti) enclosures, to prevent eddy current generation and device heating during recharge, e.g., during fast and/or high frequencies charging sessions.

The described ceramic devices may include some form of metallization to provide means for hermetic sealing of the device. However, even the presence of these metallizations used for sealing the ceramic enclosures can pose challenges with induced current generation, e.g., for small, deep IMDs. According to the techniques of this disclosure, the arrangement of metallization on the ceramic enclosure may be configured to advantageously cancel out induced currents generated therein by the time-varying magnetic fields present during recharging, thus negating the detrimental effects of these induced currents.

In some examples a medical device includes: circuitry configured to at least one of sense a physiological parameter of a patient or deliver a therapy to the patient; and a housing configured to house the circuitry. The housing includes a plurality of structural members and an attachment mechanism that joins the plurality of structural members, wherein the attachment mechanism is configured to suppress induced currents in the housing when the medical device is exposed to a time-varying magnetic field.

In some examples a method includes forming a housing configured to house circuitry of a medical device, comprising: forming a plurality of structural members; forming an attachment mechanism on the plurality of structural members; and joining the plurality of structural members using the attachment mechanism, wherein the attachment mechanism is configured to suppress induced currents in the housing when the medical device is exposed to a time-varying magnetic field.

In some examples, a medical device includes: circuitry configured to at least one of sense a physiological parameter of a patient or deliver a therapy to the patient; a rechargeable power source configured to power the circuitry; and a housing configured to house the circuitry and the power source. The housing may include: a plurality of ceramic structural members; and one or more metallizations brazed onto the plurality of structural members, wherein the one or more metallizations are welded together to join and hermetically seal the plurality of structural members, and wherein the geometry of the metallizations is configured to suppress induced currents in the housing when the medical device is exposed to a time-varying magnetic field to recharge the rechargeable power source.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

The use of rechargeable batteries or other rechargeable power sources that can be located within an IMD and utilized to power the operation of the device is becoming common to overcome the issues of limited energy primary batteries. A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to provide additional features and functions that may otherwise be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery.

However, use of rechargeable batteries or other rechargeable power sources may include additional technical challenges, especially if the device is implanted deep (e.g., more than three centimeters) within the body of a patient. Fast recharge of small, implanted devices may be accomplished via transdermal, magnetic induction when the device is implanted for example within a chamber of the heart of a patient. Electric currents may be induced in metal portions of the housing of the IMD, where energy from the induced currents is converted into heat due to the resistance of the metal portions of the housing of the IMD. This heat may damage patient tissue adjacent the medical device, even in shallowly-implanted medical devices. Generally, the stronger the time-time-varying magnetic field, the more current is induced, and the more excess heat is imparted in patient tissue. However, the deeper the IMD is within the patient's body, and the faster one desires to charge the IMD, the stronger the time-time-varying magnetic field may need to be.

The systems, devices, and methods described herein provide a way to allow the housing of an IMD to suppress induced current generation, and thereby suppress heating and damage to patient tissue. Suppressing induced current generation will further allow a magnetic field(s) to efficiently induce electrical energy (e.g., an electrical current) into the circuitry of the IMD. The induced electrical energy may be used to recharge a power source of the implanted medical device using the externally provided magnetic field, and/or to power electronic circuitry included within or coupled to the implanted medical device, including devices that may be considered deeply implanted within the patient, (e.g., devices implanted more than two to three centimeters below the skin or outer surface of the patient).

Figure 1:
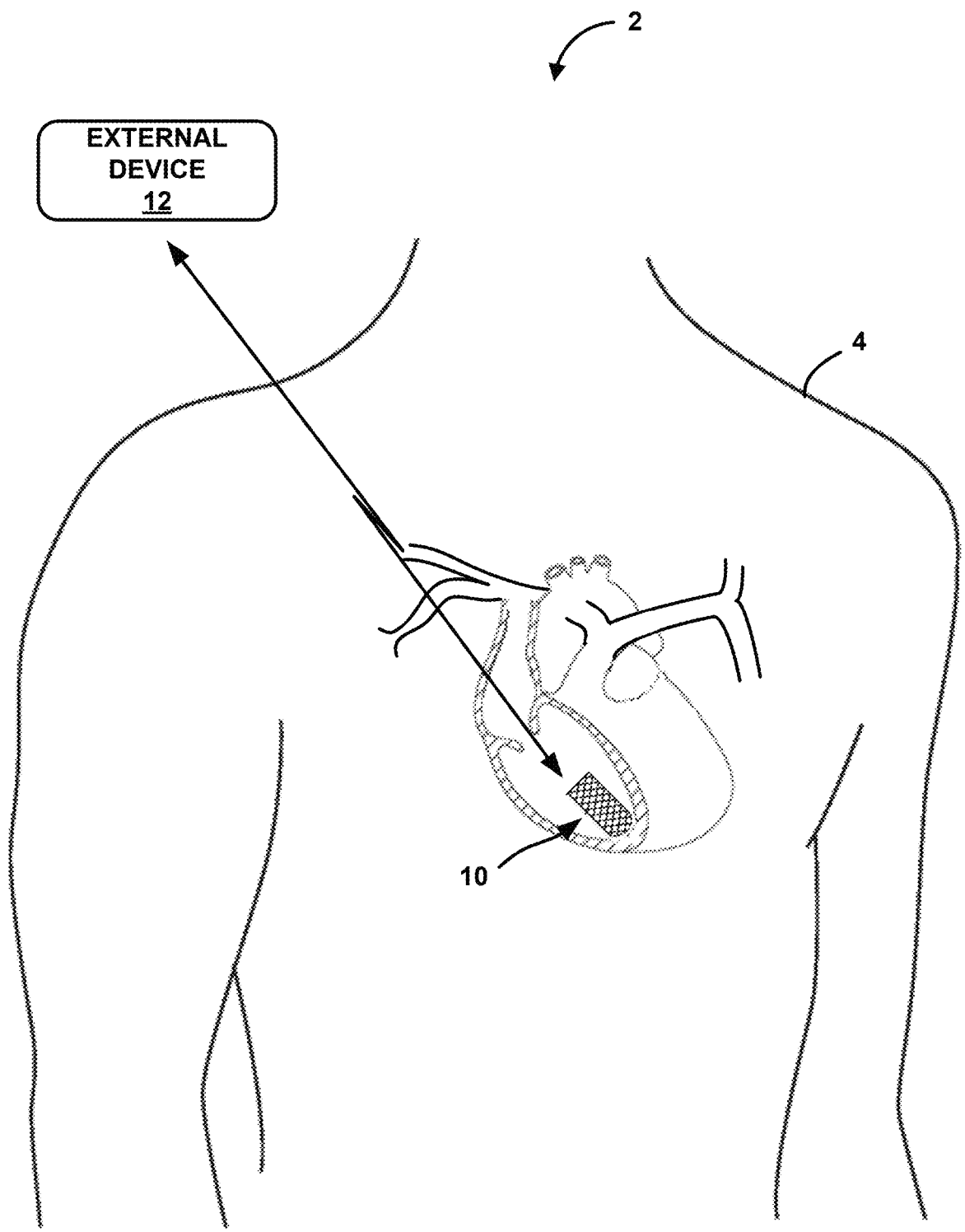
FIG. 1 illustrates the environment of an example medical device system in conjunction with a patient, in accordance with one or more techniques of this disclosure.

FIG. 1 illustrates the environment of an example medical device system 2 in conjunction with a patient 4, in accordance with one or more techniques of this disclosure. The systems, devices, and methods described in this disclosure may include examples of IMD 10 with housings configured to suppress induced current generation in the housing when IMD 10 is subject to time-varying magnetic fields (e.g., during recharging of IMD 10), for examples from a transmit coil of an external device 12 that generates the time-varying magnetic fields. For purposes of this description, knowledge of cardiovascular anatomy is presumed, and details are omitted except to the extent necessary or desirable to explain the context of the techniques of this disclosure. The systems, devices, and methods described herein may suppress induced current generation in the housing of IMD 10 when IMD 10 is subject to time time-varying magnetic fields, e.g., for the purpose of fast and efficient recharging of a power source to the electrical circuitry that is internal to IMD 10, even when IMD 10 is deeply implanted within the patient.

In various examples, IMD 10 may represent examples of a defibrillator, a cardiac resynchronization pacer/defibrillator, or a pacemaker. In the illustrated example, IMD 10 is an intracardiac and/or leadless pacemaker, such as the Micra™ transcatheter pacing system, available from Medtronic, Inc. of Minneapolis, MN. In some examples, IMD 10 is implanted outside of a thoracic cavity of patient 4 (e.g., subcutaneously in the pectoral location). IMD 10 may be positioned near the sternum near or just below the level of patient 4's heart, e.g., at least partially within the cardiac silhouette. In other examples, IMD 10 may be implanted within the cranium, thoracic cavity, abdominal cavity, an organ such as within the brain, digestive system, the heart, blood vessels, or any other internal body location. In some examples, IMD 10 takes the form of any combination of implantable cardiac devices (ICDs) with intravascular or extravascular leads, pacemakers, cardiac resynchronization therapy devices (CRT-Ds), neuromodulation devices, left ventricular assist devices (LVADs), implantable sensors, cardiac resynchronization therapy pacemakers (CRT-Ps), implantable pulse generators (IPGs), orthopedic devices, or drug pumps, as examples. IMD 10 includes a hermetically sealed housing that encloses and protects IMD 10 electronic circuitry from body fluids.

Circuitry of IMD 10, in some examples, may include one or more processors that are configured to implement functionality and/or process instructions for execution within IMD 10. For example, circuitry of IMD 10 may be capable of processing instructions stored in a memory. Circuitry may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, circuitry of IMD 10 may include any suitable structure, whether in hardware, software, firmware, or any combination thereof, to perform the functions ascribed herein to the circuitry. The circuitry may be connected to a rechargeable power supply of IMD 10.

Circuitry of IMD 10 may be configured to sense a physiological parameter of patient 4. For example, circuitry may include a number of sensors such as electrodes, optical sensors, chemical sensors, temperature sensors, acoustic sensors, motion sensors and others. Physiological parameters of a patient may include a heart rate, a glucose level, an oxygen level, a body temperature, a breathing rate, an acceleration, or other parameters of patient 4.

Circuitry may be configured to deliver a therapy to patient 4. For example, circuitry may be configured to provide neuro stimulation therapy to a spinal cord of patient 4, provide pacing therapy to a heart of patient 4, deliver controlled chemical therapy to patient 4, or provide other types of therapy to patient 4.

IMD 10 includes a power source that includes at least one rechargeable cell for powering the various circuitry of IMD 10. In some examples, IMD 10 is powered solely from the rechargeable cell and in other examples a non-rechargeable cell may be included in addition to the rechargeable cell as a backup. By including a rechargeable cell, the functional life of IMD 10 may be extended by transmitting power to IMD 10 for recharging the rechargeable cell as needed. The overall size of IMD 10 may be reduced by including the rechargeable cell for providing at least a portion of the IMD 10 power requirements. The size of the non-rechargeable backup cell can be significantly reduced in size or eliminated by including the rechargeable cell.

The rechargeable power source of IMD 10 may be recharged by a time-varying magnetic field produced by external device 12. The housing of IMD 10 includes at least a portion formed of an electromagnetically transparent material for promoting efficient power transmission to a receiving coil enclosed within housing. The receiving coil may include a multi-axis coil inside IMD 10 configured to allow recharge in multiple orientations.

External device 12 may be capable of generating a time-varying magnetic field configured to recharge the rechargeable power source of IMD 10. For example, external device 12 may be an external charging unit that includes a power source, a power transfer control unit, a transmitting coil, and a near-field focusing plate. The power source may be an AC power source, a primary battery, or a rechargeable battery. The power transfer control unit is configured to convert a power supply signal from the power source to a drive signal applied to the transmitting coil. The transmitting coil may be a single turn coil or include multiple turns and can also be made of multiple coils for impedance matching purposes for optimizing power transfer.

In some examples, the drive signal applied to the transmitting coil may have a frequency configured to keep tissue losses negligible, and produces an electromagnetic field that is focused by the near-field focusing plate. The near-field focusing plate may include focusing structures, e.g., linear structures or azimuthal structures that may be micromachined or printed structures. The focusing structures may include combination of capacitive and/or inductive elements that collectively provide a surface reactance of the near-field focusing plate that produces a subwavelength focal pattern. The focusing structures of the near-field plate converge the electromagnetic field lines induced by the drive signal applied to the transmitting coil to a linear or spot focal pattern in a focal plane at the target receiving coil within the housing of IMD 10.

The housing of IMD 10 is configured to house the circuitry and power source of IMD 10. The housing may include a plurality of structural members and an attachment mechanism that joins the plurality of structural members. At least a portion of the structural members of IMD 10 is formed of an electromagnetically transparent material for promoting efficient power transmission to the receiving coil enclosed within the housing. In some examples, the plurality of structural members are formed entirely of materials that are transparent to radiative electromagnetic energy. For example, the plurality of structural members may be formed from ceramic, glass, polymeric material, or other electromagnetically transparent material. In this manner, the time-varying magnetic fields produced by external device 12 to charge the power source of IMD 10 may pass through the structural members without inducing any current in the structural members. The lack of current in the structural members will allow the power source of IMD 10 to be recharged quickly, and with high frequency time-varying magnetic fields without unduly heating the structural members of IMD 10 and causing damage to tissue of patient 4.

The plurality of structural members may be joined by the attachment mechanism. In some examples, the attachment mechanism is a conductive material. For example, the attachment mechanism may be one or more metallizations that are bonded or sealed onto each of the plurality of structural members. For example, the attachment mechanism may be attached to the plurality of structural members using a ferrule and brazing techniques or other bonding or sealing methods. The metallizations attached to each of the plurality of structural members may be welded to one another to form a hermetic seal between the plurality of structural members, and form the housing of IMD 10. The welds may be accomplished through any welding process, such as laser welding. The attachment mechanism may be configured to suppress induced currents in the housing when the medical device is exposed to a time-varying magnetic field, for example a time-varying magnetic field to recharge the rechargeable power source.

In some examples, the attachment mechanism may comprise a conductive material, and the geometry of the attachment mechanism on the housing of IMD 10 may cause opposing currents to be generated within the conductive material when IMD 10 is exposed to a time-varying magnetic field. The geometry of the attachment mechanism may define a contiguous path around the housing such that the path forms two partial loops around one or more axes of the medical device.

Throughout the disclosure reference is made to a "magnetic field" or to "magnetic fields" in the context of a magnetic field or magnetic fields that is/are generated externally to an implantable medical device, and imposed onto the implanted medical device for the purpose of inducing a current into the circuitry of the implantable medical device. Any magnetic field or magnetic fields having a parameter (e.g., amplitude or phase) of the magnetic field that varies in time, or that varies in time with respect to the magnetic field direction of the magnetic field, such that a time rate of change of the net magnetic flux intensity imposed onto the coil windings of the receive antenna configuration, and a corresponding change in the electro-motive force (emf) configured to generate a current or currents in the one or more coil windings is contemplated by the use of the terms "magnetic field" and "magnetic fields" throughout this disclosure.

Figure 2:
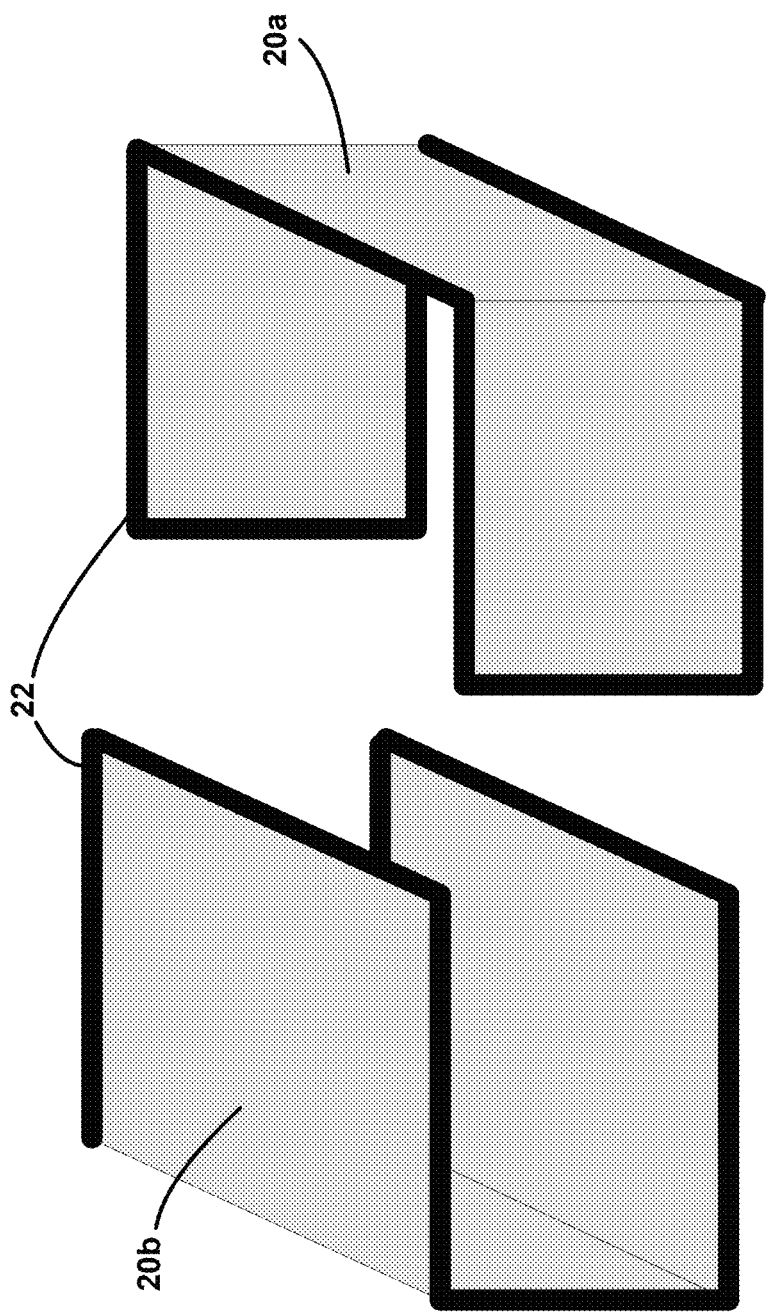
FIG. 2 is a schematic diagram of one embodiment of housing of an IMD before assembly of the IMD.

FIG. 2 is a schematic diagram of one embodiment of housing of an IMD before assembly of the IMD. The housing includes a first structural member 20a, a second structural member 20b (structural members 20), and attachment mechanism 22. Structural members 20 may be joined by attachment mechanism 22 to form a housing around the power source and circuitry of the assembled IMD.

Structural members 20 may be formed of an electromagnetically transparent material for promoting efficient power transmission the circuitry and power source of the IMD. For example, structural members 20 may be formed from ceramic, glass, polymeric material, or other electromagnetically transparent material. Structural members 20 may be formed by any known process or method, for example subtractive manufacturing, where a solid block of material is machined away until structural members 20 remain. In some examples, structural members 20 may be manufactured through an additive process, where thin layers of material are deposited in the desired shape until structural members 20 are formed. In some examples, structural members 20 may be formed through green tape ceramic manufacturing processes.

The plurality of structural members may be joined by attachment mechanism 22. Attachment mechanism 22 may be a conductive material. For example, attachment mechanism 22 may be one or more metallizations that are bonded or sealed onto each of structural members 20. For example, attachment mechanism 22 may be attached to structural members 20 using a ferrule and brazing techniques or other bonding or sealing methods. Attachment mechanism 22 may be attached to structural members 20 at one or more edges of structural members 20. For example, as shown in FIG. 2, a profile of structural members 20 may define a cuboid, and attachment mechanism 22 may be attached to one or more edges of each of structural members 20. Structural members 20 may be joined together by attachment mechanism 22 at the one or more edges where attachment mechanism 22 is attached to each of structural members 20.

Attachment mechanism 22 on structural member 20*a* may be laser welded to attachment mechanism 22 on structural member 20*b* along the one or more edges of structural members 20 to form a hermetic seal between structural members 20, and form the housing of IMD 10. The geometry of attachment mechanism 22 as it extends along the one or more edges of structural members 20 may cause opposing currents to be generated within the conductive material of attachment mechanism 22 when the housing is exposed to a time-varying magnetic field.

Although only two structural members are shown in FIG. 2, the housing may include more structural members, where each of the structural members are joined to one another by an attachment mechanism configured to suppress induced currents in the housing when the medical device is exposed to a time-varying magnetic field as described throughout the disclosure. The attachment mechanism may include multiple materials, where some materials are conductive, and others are electromagnetically transparent. The structural members may be joined by both the conductive and the electromagnetically transparent materials in different places, such that the geometry of the conductive material in the attachment mechanism is formed as described in examples in this disclosure.

Figure 3:
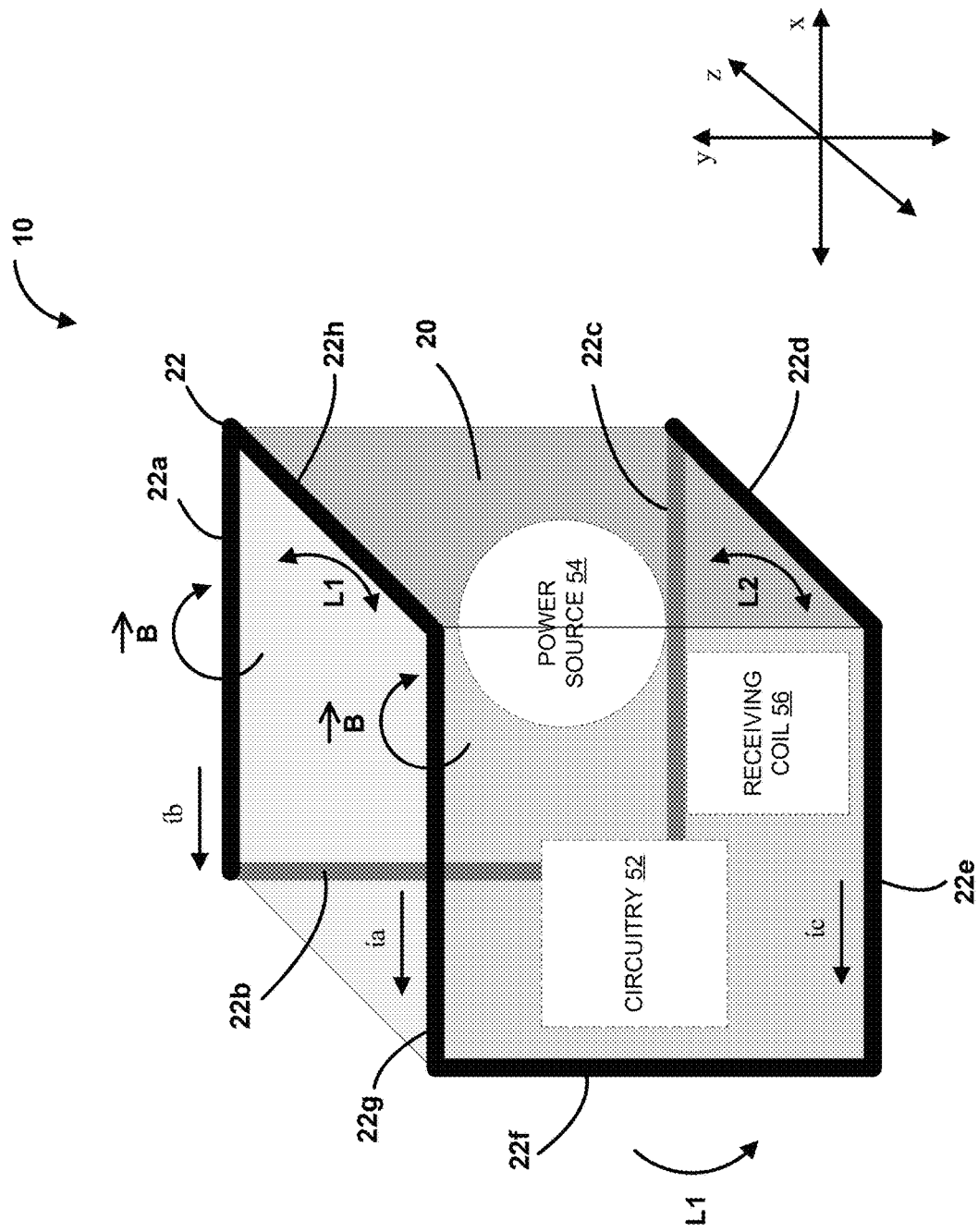
FIG. 3 is a schematic diagram of an IMD with the housing of FIG. 2 configured to suppress induced currents.

FIG. 3 is a schematic diagram of IMD 10 with the housing of FIG. 2 configured to suppress induced currents. IMD 10 includes power source 54, circuitry 52, receiving coil 56, and a housing including structural members 20 and attachment mechanism 22. Circuitry 52, receiving coil 56, and power source 54 are contained inside the hermetically sealed housing of IMD 10. Attachment mechanism 22 may be conceptually divided into eight attachment mechanism segments 22*a-h*. Segments 22*b* and 22*c* are shown on the opposite side of IMD 10 for ease of description. Each segment 22*a-h* extends along an edge of IMD 10 from one corner of IMD 10 to another.

The housing of IMD 10 defines a cuboid as shown in FIG. 3. The structural members 20 are joined together by attachment mechanism 22 at the edges of the cuboid. The geometry of attachment mechanism 22 may define a contiguous path around the housing along one or more edges of the cuboid. Attachment mechanism 22 may be made of a conductive material, for example a metallization, wherein the geometry of attachment mechanism 22 causes opposing currents to be generated within the conductive material when IMD 10 is exposed to a time-varying magnetic field.

The geometry of attachment mechanism 22 may define a contiguous path around the housing such that the path forms two partial loops around one or more axes of the medical device. For example, segments 22*a*, 22*g*, and 22*h* of attachment mechanism 22 may form a first partial loop $L_1$ around a y-axis of IMD 10 as shown in FIG. 3. Similarly, segments 22*c*, 22*d*, and 22*e* may form a second partial loop $L_2$ around the y-axis of IMD 10. As evidenced by FIG. 3, the partial loops need not have rounded corners. In some examples, segments 22*e*, 22*f*, and 22*g* may form a first partial loop around a z-axis of IMD 10 as shown in FIG. 3. Similarly, segments 22*a*, 22*b*, and 22*c* may form a second partial loop around the z-axis of IMD 10. The nomenclature of the axes is used here for illustrative purposes only.

Due to this geometric arrangement, opposing currents may be induced in attachment mechanism 22 that cancel one another out when IMD 10 is exposed to a time-varying magnetic field arranged in multiple orientations. For example, if IMD 10 is subject to a time-varying magnetic field $\vec{B}$ directed in a positive-z direction as shown in FIG. 3, a first current $i_a$ may be induced counterclockwise in the first partial loop around the z-axis defined by segments 22*e*, 22*f*, and 22*g*. The same time-varying magnetic field $\vec{B}$ may also induce a second current $i_b$ counterclockwise in the second partial loop around the z axis defined by segments 22*a*, 22*b*, and 22*c*. Because attachment mechanism 22 defines a contiguous path, the first and second partial loops are connected in the same circuit, thus the first and second currents oppose one another and cancel one another out.

In a similar manner, if IMD 10 is subject to a time-varying magnetic field $\vec{B}$ directed in a positive y-direction as shown in FIG. 3, a first current $i_a$ may be induced in the first partial loop around the y-axis defined by segments 22*a*, 22*g*, and 22*h*. For example, first current $i_a$ may travel in a negative x-direction on segment 22*g* when traveling around the first partial loop defined by segments 22*a*, 22*g*, and 22*h*. The same time-varying magnetic field $\vec{B}$ may also induce a second current $i_c$ in the second partial loop around the y-axis defined by segments 22*c*, 22*d*, and 22*e*. For example, second current $i_c$ may travel in a negative x-direction on segment 22*e* when traveling around the second partial loop defined by segments 22*c*, 22*d*, and 22*e*. The first and second currents may have roughly equivalent magnitudes (i.e., electromotive forces). Because attachment mechanism 22 defines a contiguous path, the first and second partial loops are connected in the same circuit, thus the first and second currents oppose one another and cancel one another out.

In some examples, if IMD 10 is subject to a time-varying magnetic field B directed in an x-direction, a current may be induced around attachment mechanism 22 without being canceled. When viewing a two-dimensional profile of attachment mechanism 22 from an x-direction, attachment mechanism 22 makes a full loop around the x-axis, where the full loop includes segments 22*h*, 22*f*, 22*d*, and 22*b*. Segments 22*a*, 22*c*, 22*e*, and 22*g* are parallel with the x-axis, thus parallel with the magnetic flux of the time-varying magnetic field B, and may not contribute to any induced current. It may therefore be advantageous to design IMD 10 to present the smallest profile with respect to this axis to minimize induced current in attachment mechanism 22. For some IMDs, the orientation of the IMD, and thus the orientation of a housing configured to suppress induced currents may not be precisely known, or may shift at some point in time after implantation of IMD 10 into patient 4. This shifting of position may include movement of IMD 10 itself during the time when recharging of IMD 10 is being performed. Such shift in position may be caused by motions of tissue in the area of the implantation, such as cardiac activity including heartbeats of the heart of patient 4, and/or movements of patient 4 themselves, such as when patient 4 is walking, standing, or changing position, including patient movements while patient 4 is lying down. Such changes in orientation of IMD 10 may cause issues, including induced current generation in unpredictable portions of the IMD 10 housing, while attempting to inductively recharge a power source, such as a battery, that is located within IMD 10. By forming the housing of IMD 10 as described above, opposing induced currents will be formed and cancel out in multiple orientations and avoid issues arising with unknown housing orientation.

Because of the geometry of attachment mechanism 22, a time-varying magnetic field may charge the rechargeable power source 54 of IMD 10 by inducing a current in receiving coil 56 and powering circuitry 52, without generating excess induced currents in the housing, and subsequently excess heat that could cause harm to the patient.

Figure 4:
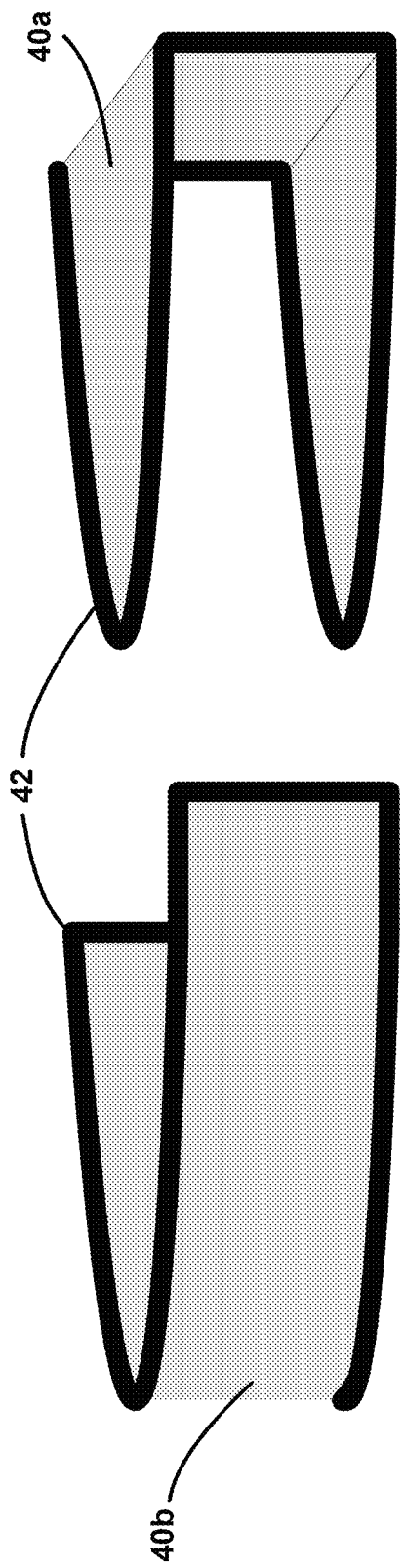
FIG. 4 is a schematic diagram of another embodiment of the housing of an IMD before assembly of the IMD.

FIG. 4 is a schematic diagram of another embodiment of the housing of an IMD before assembly of the IMD. before assembly of the IMD. The housing includes a first structural member 40a, a second structural member 40b (structural members 40), and attachment mechanism 42. Structural members 40 may be joined by attachment mechanism 42 to form a housing around the power source and circuitry of the assembled IMD.

Structural members 40 may be formed of an electromagnetically transparent material for promoting efficient power transmission the circuitry and power source of the IMD. For example, structural members 40 may be formed from ceramic, glass, polymeric material, or other electromagnetically transparent material. Structural members 40 may be formed by any known process or method, for example subtractive manufacturing, where a solid block of material is machined away until structural members 40 remain. In some examples, structural members 42 may be manufactured through an additive process, where thin layers of material are deposited in the desired shape until structural members 40 are formed. In some examples, structural members 42 may be formed through green tape ceramic manufacturing processes.

The plurality of structural members may be joined by attachment mechanism 42. Attachment mechanism 42 may be a conductive material. For example, attachment mechanism 42 may be one or more metallizations that are bonded or sealed onto each of structural members 40. For example, attachment mechanism 42 may be attached to structural members 40 using a ferrule and brazing techniques or other bonding or sealing methods. Attachment mechanism 42 may be attached to structural members 40 at one or more edges of structural members 40. For example, as shown in FIG. 4, a profile of structural members 40 may define an extruded semioval, and attachment mechanism 42 may be attached to one or more edges of each of structural members 40. Structural members 40 may be joined together by attachment mechanism 42 at the one or more edges where attachment mechanism 42 is attached to each of structural members 40.

Attachment mechanism 42 on structural member 40a may be laser welded to attachment mechanism 42 on structural member 40b along the one or more edges of structural members 40 to form a hermetic seal between structural members 40, and form the housing of IMD 10. The geometry of attachment mechanism 42 as it extends along the one or more edges of structural members 40 may cause opposing currents to be generated within the conductive material of attachment mechanism 42 when the housing is exposed to a time-varying magnetic field.

Although only two structural members are shown in FIG. 4, the housing may include more structural members, where each of the structural members are joined to one another by an attachment mechanism configured to suppress induced currents in the housing when the medical device is exposed to a time-varying magnetic field as described throughout the disclosure. The attachment mechanism may include multiple materials, where some materials are conductive, and others are electromagnetically transparent. The structural members may be joined by both the conductive and the electromagnetically transparent materials in different places, such that the geometry of the conductive material in the attachment mechanism is formed as described in examples in this disclosure.

Figure 5:
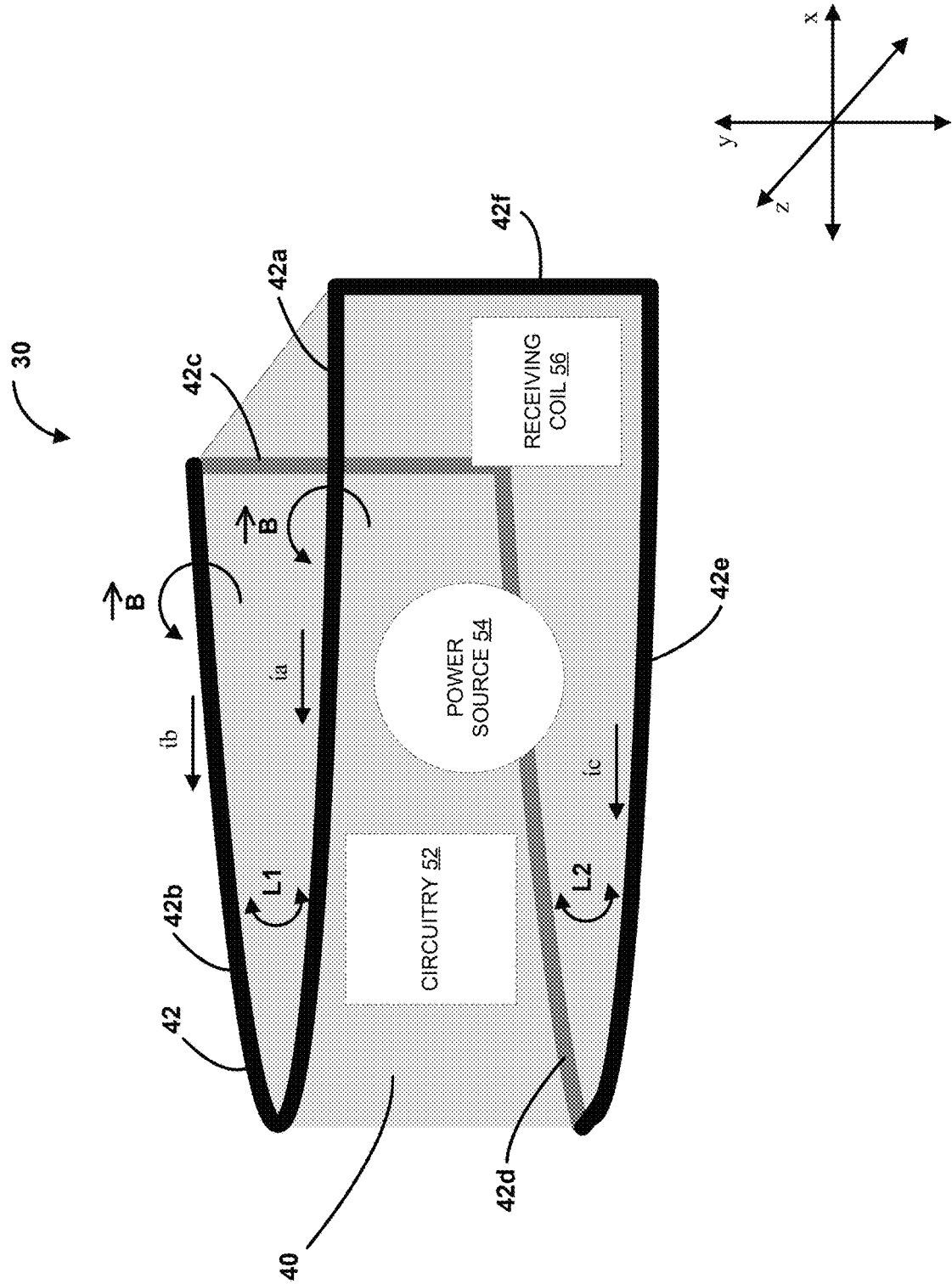
FIG. 5 is a schematic diagram of an IMD with the housing of FIG. 4 configured to suppress induced currents.

FIG. 5 is a schematic diagram of an IMD 30 with the housing of FIG. 4 configured to suppress induced currents. IMD 30 includes power source 54, circuitry 52, receiving coil 56, and a housing including structural members 40 and attachment mechanism 42. Circuitry 52, receiving coil 56, and power source 54 are contained inside the hermetically sealed housing of IMD 30. Attachment mechanism 42 may be conceptually divided into six attachment mechanism segments 42a-f. Segments 42c and 42d are shown on the opposite side of IMD 30 for ease of description. Each segment 42a-f extends along an edge of IMD 30.

The housing of IMD 30 defines an extruded semioval as shown in FIG. 5. The structural members 40 are joined together by attachment mechanism 42 at the edges of the extruded semioval. The geometry of attachment mechanism 42 may define a contiguous path around the housing along one or more edges of the extruded semioval. Attachment mechanism 42 may be made of a conductive material, for example a metallization, wherein the geometry of attachment mechanism 42 causes opposing currents to be generated within the conductive material when IMD 30 is exposed to a time-varying magnetic field.

The geometry of attachment mechanism 42 may define a contiguous path around the housing such that the path forms two partial loops around one or more axes of the medical device. For example, segments 42a and 42b of attachment mechanism 42 may form a first partial loop $L_1$ around a y-axis of IMD 30 as shown in FIG. 5. Similarly, segments 42e and 42d may form a second partial loop $L_2$ around the y-axis of IMD 30. In some examples, segments 42e, 42f, and 42a may form a first partial loop around a z-axis of IMD 30 as shown in FIG. 5. Similarly, segments 42b, 42c, and 42d may form a second partial loop around the z-axis of IMD 30. The nomenclature of the axes is used here for example only.

Due to this geometric arrangement, opposing currents may be induced in attachment mechanism 42 that cancel one another out when IMD 30 is exposed to a time-varying magnetic field arranged in multiple orientations. For example, if IMD 10 is subject to a time-varying magnetic field B directed in a positive-z direction, a first current $i_a$ may be induced counterclockwise in the first partial loop around the z-axis defined by segments 42e, 42f, and 42a. The same time-varying magnetic field B may also induce a second current $i_b$ counterclockwise in the second partial loop around the z-axis defined by segments 42b, 42c, and 42d. The first and second currents will have roughly equivalent magnitudes (i.e., electromotive forces). Because attachment mechanism 42 defines a contiguous path, the first and second partial loops are connected in the same circuit, and the first and second currents oppose one another and cancel one another out.

In a similar manner, if IMD 30 is subject to a time-varying magnetic field B directed in a positive y-direction as shown in FIG. 5, a first current $i_a$ may be induced in the first partial loop $L_1$ around the y-axis defined by segments 42a, 42b. For example, first current $i_a$ may travel in a negative x-direction on segment 42a when traveling around the first partial loop $L_1$ defined by segments 42a and 42b. The same time-varying magnetic field B may also induce a second current $i_c$ in the second partial loop $L_2$ around the y-axis defined by segments 42*d* and 42*e*. For example, second current $i_c$ may travel in a negative x-direction on segment 42*e* when traveling around the second partial loop $L_2$ defined by segments 42*d* and 42*e*. Because attachment mechanism 42 defines a contiguous path, the first and second partial loops ($L_1$ and $L_2$) are connected in the same circuit, and the first and second currents ($L_1$ and $L_2$) may oppose one another within the path and cancel one another out.

In some examples, if IMD 30 is subject to a time-varying magnetic field B directed in an x-direction, a current may be induced around attachment mechanism 42 without being canceled. When viewing a two-dimensional profile of attachment mechanism 42 from an x-direction, attachment mechanism 42 makes a full loop around the x-axis. It may therefore be advantageous to design IMD 30 to present the smallest profile with respect to this axis to minimize induced current in attachment mechanism 42.

For some IMDs, the orientation of the IMD, and thus the orientation of a housing configured to suppress induced currents may not be precisely known, or may shift at some point in time after implantation of IMD 30 into patient 4. This shifting of position may include movement of IMD 30 itself during the time when recharging of IMD 30 is being performed. Such shift in position may be caused by motions of tissue in the area of the implantation, such as cardiac activity including heartbeats of the heart of patient 4, and/or movements of patient 4 themselves, such as when patient 4 is walking, standing, or changing position, including patient movements while patient 4 is lying down. Such changes in orientation of IMD 30 may cause issues, including induced current generation in unpredictable portions of the IMD 30 housing, while attempting to inductively recharge a power source, such as a battery, that is located within IMD 30. By forming the housing of IMD 30 as described above, opposing induced currents will be formed and cancel out in multiple orientations and avoid issues arising with unknown housing orientation.

Because of the geometry of attachment mechanism 42, a time-varying magnetic field may charge the rechargeable power source 54 of IMD 30 by inducing a current in receiving coil 56 and powering circuitry 52, without generating excess induced currents in the housing, and subsequently excess heat that could cause harm to the patient.

Although FIGS. 2-5 depict a cuboid or an extruded semioval shape for the housing of the IMD, other shapes for the housing are contemplated, and other geometries of the attachment mechanism, such that the geometry of the attachment mechanism causes opposing currents to be generated within the conductive material of the attachment mechanism when the IMD is exposed to time-varying magnetic fields. For example, the housing may define a sphere or spheroid, wherein the attachment mechanism joins the plurality of structural members along a seam of the spheroid. The geometry of the attachment mechanism around the spheroid may define a contiguous path such that the path forms two partial loops around one or more axes of the medical device. For example, the attachment mechanism may be disposed in a geometry on the spheroid like that of the stitching on a baseball. Similarly, the housing may define other shapes such as a cylinder, a triangular or other prism, a dodecahedron or other polyhedron, etc. where the geometry of the attachment mechanism defines a contiguous path around the housing such that the path forms two partial loops around one or more axes of the medical device.

Figure 6:
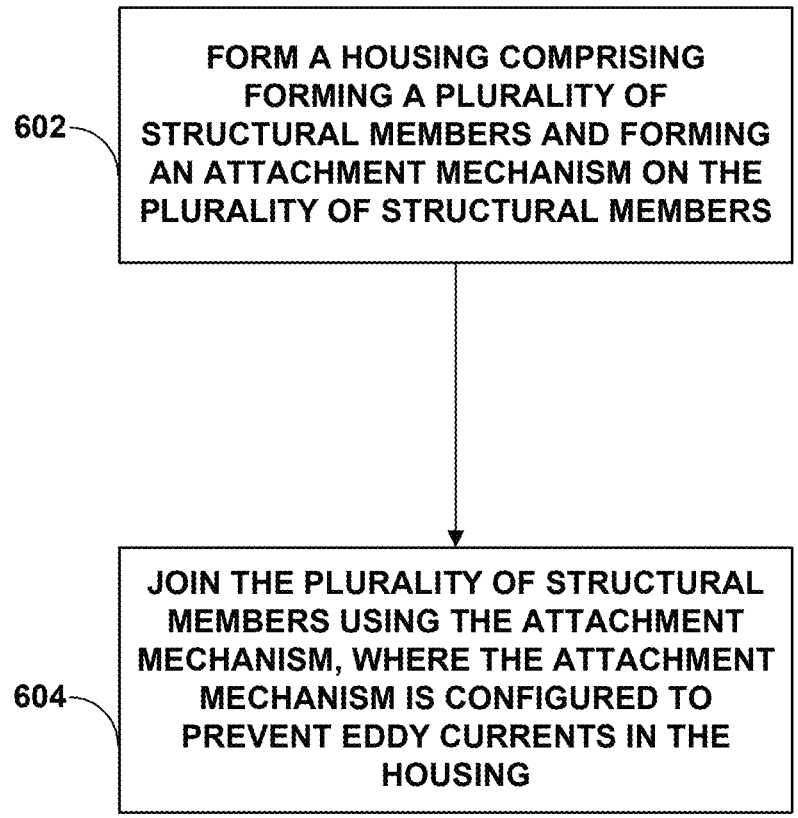
FIG. 6 is a flow diagram illustrating an example method of forming a medical device housing.

FIG. 6 is a flow diagram illustrating an example method of forming a medical device housing. A method includes forming a housing configured to house circuitry and a rechargeable power source of a medical device, wherein forming the housing includes forming a plurality of structural members and forming an attachment mechanism on the plurality of structural members (602).

The medical device may be an IMD, such as a defibrillator, a cardiac resynchronization pacer/defibrillator, or a pacemaker, etc. In some examples, the IMD takes the form of any combination of implantable cardiac devices (ICDs) with intravascular or extravascular leads, pacemakers, cardiac resynchronization therapy devices (CRT-Ds), neuromodulation devices, left ventricular assist devices (LVADs), implantable sensors, cardiac resynchronization therapy pacemakers (CRT-Ps), implantable pulse generators (IPGs), orthopedic devices, or drug pumps, as examples.

The circuitry of the IMD may be configured to sense a physiological parameter of a patient, deliver a therapy to a patient, or both. In some examples, circuitry may include a number of sensors such as electrodes, optical sensors, chemical sensors, temperature sensors, acoustic sensors, motion sensors and others. Physiological parameters of a patient may include a heart rate, a glucose level, an oxygen level, a body temperature, a breathing rate, an acceleration, or other parameters of the patient. In some examples, circuitry may be configured to provide neuro stimulation therapy to a spinal cord of the patient, provide pacing therapy to a heart of the patient, deliver controlled chemical therapy to the patient, or provide other types of therapy to the patient.

The IMD may include a rechargeable power source for powering the various circuitry of the IMD. The rechargeable power source may be recharged by a time-varying magnetic field produced externally from the IMD.

Forming the plurality of structural members may include forming the plurality of structural members from a material that is transparent to radiative electromagnetic energy. The electromagnetically transparent material may promote efficient power transmission from the time-varying magnetic field to a receiving coil enclosed within the housing. For example, the plurality of structural members may be formed from ceramic, glass, polymeric material, or other electromagnetically transparent material. In this manner, the time-varying magnetic fields produced externally that charge the power source of the IMD may pass through the structural members without inducing any current in the structural members. The lack of current in the structural members will allow the power source of the IMD to be recharged quickly, and in high frequency time-varying magnetic fields without unduly heating the structural members, which could cause damage to tissue of the patient. The structural members may be formed by any known process or method, for example subtractive manufacturing, where a solid block of material is machined away until the structural members remain. In some examples, the structural members may be manufactured through an additive process, where thin layers of material are deposited in the desired shape until the structural members are formed. In some examples, the structural members may be formed through green tape ceramic manufacturing processes.

Forming an attachment mechanism on the plurality of structural members may include forming a conductive material onto the plurality of structural members. For example, the attachment mechanism may be formed by bonding or sealing one or more metallizations onto each of the plurality of structural members. In some examples, the attachment mechanism may be attached to the plurality of structural members using a ferrule and brazing techniques or other bonding or sealing methods.

Once formed onto the plurality of structural members, the attachment mechanism may define a geometry, wherein the geometry of the conductive material on the structural members causes opposing currents to be generated within the conductive material when the medical device is exposed to a time-varying magnetic field. For example, the attachment mechanism may be made of a conductive material defining a contiguous path around the structural members. A time-varying magnetic field may induce a current in multiple segments of the continuous path at once, where the induced current in the multiple segments is traveling in opposite directions along the contiguous path.

The method further includes joining the plurality of structural members using the attachment mechanism, wherein the attachment mechanism are configured to suppress induced currents in the housing when the medical device is exposed to a time-varying magnetic field, for example a time-varying magnetic field to recharge the rechargeable power source (604).

In some examples, the attachment mechanism includes one or more metallizations attached to each of the plurality of structural members that may be welded to one another to form a hermetic seal between the plurality of structural members, and to form the housing of the IMD. The welds may be accomplished through any welding process, such as laser welding.

Joining the plurality of structural members may include joining the plurality of structural members into a cuboid shape, an extruded semioval shape, a spheroid shape, or other shape. The plurality of structural members may be joined at one or more edges of the cuboid or the extruded semioval using the attachment mechanism, and may be joined at a seam of the spheroid. The geometry of the attachment mechanism may define a contiguous path around the edge of the shape, and the geometry of the attachment mechanism around the edges of the shape may cause opposing currents to be generated within the conductive material when the medical device is exposed to a time-varying magnetic field.

The geometry of the attachment mechanism may define a contiguous path around the housing such that the path forms two partial loops around one or more axes of the medical device. For example, the attachment mechanism 22 of FIG. 3 may form two partial loops around a y-axis. With reference to FIG. 3, segments 22a, 22g, and 22h of attachment mechanism 22 may form a first partial loop $L_1$ around a y-axis of IMD 10 as shown in FIG. 3. Similarly, segments 22c, 22d, and 22e may form a second partial loop $L_2$ around the y-axis of IMD 10. As evidenced by FIG. 3, the partial loops need not have rounded corners. In some examples, the attachment mechanism 42 of FIG. 5 may form two partial loops around a y-axis. With reference to FIG. 5, segments 42a and 42b of attachment mechanism 42 may form a first partial loop $L_1$ around a y-axis of IMD 30 as shown in FIG. 5. Similarly, segments 42e and 42d may form a second partial loop $L_2$ around the y-axis of IMD 30.

The geometry of the contiguous attachment mechanism around the shape may cause opposing currents to be generated within the conductive material of the attachment mechanism when the medical device is exposed to a time-varying magnetic field. In some examples, with reference to FIG. 3 where the shape is a cuboid, IMD 10 may be subject to a time-varying magnetic field B directed in a positive-z direction. The geometry of attachment mechanism 22 may allow a first current $i_a$ to be induced counterclockwise in the first partial loop around the z-axis defined by segments 22e, 22f, and 22g because of the time-varying magnetic field B, and a second current is to be induced counterclockwise in the second partial loop around the z-axis defined by segments 22a, 22b, and 22c by the same time-varying magnetic field B. Because attachment mechanism 22 defines a contiguous path, the first and second currents oppose one another and cancel one another out. In some examples, with reference to FIG. 5 where the shape is an extruded semioval, IMD 30 may be subject to a time-varying magnetic field $\vec{B}$ directed in a positive z-direction. The geometry of attachment mechanism 42 may allow a first current $i_a$ to be induced counterclockwise in the first partial loop around the z-axis defined by segments 42e, 42f, and 42a because of the time-varying magnetic field B, and a second current $i_b$ to be induced counterclockwise in the second partial loop around the z-axis defined by segments 42b, 42c, and 42d by the same time-varying magnetic field B. The first and second currents will have roughly equivalent magnitudes (i.e., electromotive forces). Because attachment mechanism 42 defines a contiguous path, the first and second currents oppose one another and cancel one another out. Aspects of this disclosure includes the following examples.

Example 1: A medical device includes: circuitry configured to at least one of sense a physiological parameter of a patient or deliver a therapy to the patient; and a housing configured to house the circuitry. Wherein the housing includes: a plurality of structural members; and an attachment mechanism that joins the plurality of structural members, wherein the attachment mechanism is configured to suppress induced currents in the housing when the medical device is exposed to a time-varying magnetic field.

Example 2: The medical device of example 1, wherein the attachment mechanism includes a conductive material, and wherein the geometry of the attachment mechanism causes opposing currents to be generated within the conductive material when the medical device is exposed to the time-varying magnetic field.

Example 3: The medical device of example 2, wherein the geometry of the attachment mechanism defines a contiguous path around the housing such that the path forms two partial loops around one or more axes of the medical device.

Example 4: The medical device of any of examples 1-3, wherein the housing defines a cuboid, and wherein the attachment mechanism joins the plurality of structural members at one or more edges of the cuboid.

Example 5: The medical device of any of examples 1-3, wherein the housing defines an extruded semioval, and wherein the attachment mechanism joins the plurality of structural members at one or more edges of the extruded semioval.

Example 6: The medical device of any of examples 1-3, wherein the housing defines a spheroid, and wherein the attachment mechanism joins the plurality of structural members along a seam of the spheroid.

Example 7: The medical device of any of examples 1-6, wherein the attachment mechanism includes one or more metallizations that are laser welded to join the plurality of structural members.

Example 8: The medical device of example 7, wherein the one or more metallizations are brazed onto the plurality of structural members.

Example 9: The medical device of example 8, wherein the one or more metallizations are diffusion bonded onto the plurality of structural members.

Example 10: The medical device of any of examples 1-9, wherein the plurality of structural members are transparent to radiative electromagnetic energy.

Example 11: The medical device of example 10, wherein the plurality of structural members comprise at least one of a ceramic material, a glass material, or a polymeric material.

Example 12: The medical device of any of examples 1-11, wherein the housing is hermetically sealed.

Example 13: The medical device of any of examples 1-12, further including a rechargeable power source housed within the housing and configured to power the circuitry, wherein the time-varying magnetic field is configured to recharge the rechargeable power source.

Example 14: A method includes forming a housing configured to house circuitry of a medical device, including: forming a plurality of structural members; forming an attachment mechanism on the plurality of structural members; and joining the plurality of structural members using the attachment mechanism, wherein the attachment mechanism is configured to suppress induced currents in the housing when the medical device is exposed to a time-varying magnetic field Example 15: The method of example 14, wherein forming the attachment mechanism on the plurality of structural members includes forming a conductive material onto the plurality of structural members defining a geometry, wherein the geometry of the conductive material on the structural members causes opposing currents to be generated within the conductive material when the medical device is exposed to a time-varying magnetic field.

Example 16: The method of example 15, wherein the geometry of the attachment mechanism defines a contiguous path around the housing such that the path forms two partial loops around one or more axes of the medical device.

Example 17: The method of examples 14 or 15, wherein joining the plurality of structural members includes: joining the plurality of structural members into a cuboid shape; and joining the structural members at one or more edges of the cuboid using the attachment mechanism.

Example 18: The method of examples 14 or 15, wherein joining the plurality of structural members includes: joining the plurality of structural members into an extruded semioval shape; and joining the structural members at one or more edges of the extruded semioval using the attachment mechanism.

Example 19: The method of examples 14 or 15, wherein joining the plurality of structural members includes: joining the plurality of structural members into a spheroid shape; and joining the structural members along a seam of the spheroid using the attachment mechanism.

Example 20: The method of any of examples 14-19, wherein forming the attachment mechanism on the plurality of structural members includes brazing one or more metallizations onto the plurality of structural members.

Example 21: The method of any of examples 14-20, wherein the plurality of structural members are transparent to radiative electromagnetic energy.

Example 22: The method of any of examples 14-21, wherein the housing is configured to house a rechargeable power source configured to power the circuitry, and wherein the time-varying magnetic field is configured to recharge the rechargeable power source.

Example 23: A medical device including: circuitry configured to at least one of sense a physiological parameter of a patient or deliver a therapy to the patient; a rechargeable power source configured to power the circuitry; and a housing configured to house the circuitry and the power source, wherein the housing includes: a plurality of ceramic structural members; and one or more metallizations brazed onto the plurality of structural members, wherein the one or more metallizations are welded together to join and hermetically seal the plurality of structural members, and wherein the geometry of the metallizations is configured to suppress induced currents in the housing when the medical device is exposed to a time-varying magnetic field to recharge the rechargeable power source.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device comprising:
   circuitry configured to at least one of sense a physiological parameter of a patient or deliver a therapy to the patient; and
   a housing configured to house the circuitry, wherein the housing comprises:
      a plurality of structural members; and
      an attachment mechanism that joins the plurality of structural members, wherein the attachment mechanism is configured to suppress induced currents in the housing when the medical device is exposed to a time-varying magnetic field.

2. The medical device of claim 1, wherein the attachment mechanism comprises a conductive material, and wherein the geometry of the attachment mechanism causes opposing currents to be generated within the conductive material when the medical device is exposed to the time-varying magnetic field.

3. The medical device of claim 2, wherein the geometry of the attachment mechanism defines a contiguous path around the housing such that the path forms two partial loops around one or more axes of the medical device.

4. The medical device of claim 1, wherein the housing defines a cuboid, and wherein the attachment mechanism joins the plurality of structural members at one or more edges of the cuboid.

5. The medical device of claim 1, wherein the housing defines an extruded semioval, and wherein the attachment mechanism joins the plurality of structural members at one or more edges of the extruded semioval.

6. The medical device of claim 1, wherein the housing defines a spheroid, and wherein the attachment mechanism joins the plurality of structural members along a seam of the spheroid.

7. The medical device of claim 1, wherein the attachment mechanism comprises one or more metallizations that are one or more of:
   laser welded to join the plurality of structural members,
   brazed onto the plurality of structural members, or
   diffusion bonded onto the plurality of structural members.

8. The medical device of claim 1, wherein the plurality of structural members are transparent to radiative electromagnetic energy.

9. The medical device of claim 1, wherein the housing is hermetically sealed.

10. The medical device of claim 1, further comprising a rechargeable power source housed within the housing and configured to power the circuitry, wherein the time-varying magnetic field is configured to recharge the rechargeable power source.

11. A method comprising:
   forming a housing configured to house circuitry of a medical device, comprising:
      forming a plurality of structural members;
      forming an attachment mechanism on the plurality of structural members; and
      joining the plurality of structural members using the attachment mechanism, wherein the attachment mechanism is configured to suppress induced currents in the housing when the medical device is exposed to a time-varying magnetic field.

12. The method of claim 11, wherein forming the attachment mechanism on the plurality of structural members comprises forming a conductive material onto the plurality of structural members defining a geometry, wherein the geometry of the conductive material on the structural members causes opposing currents to be generated within the conductive material when the medical device is exposed to a time-varying magnetic field.

13. The method of claim 12, wherein the geometry of the attachment mechanism defines a contiguous path around the housing such that the path forms two partial loops around one or more axes of the medical device.

14. The method of claim 11, wherein joining the plurality of structural members comprises:
   joining the plurality of structural members into a cuboid shape; and
   joining the structural members at one or more edges of the cuboid using the attachment mechanism.

15. The method of claim 11, wherein joining the plurality of structural members comprises:
   joining the plurality of structural members into an extruded semioval shape; and
   joining the structural members at one or more edges of the extruded semioval using the attachment mechanism.

16. The method of claim 11, wherein joining the plurality of structural members comprises:
   joining the plurality of structural members into a spheroid shape; and
   joining the structural members along a seam of the spheroid using the attachment mechanism.

17. The method of claim 11, wherein forming the attachment mechanism on the plurality of structural members comprises brazing one or more metallizations onto the plurality of structural members.

18. The method of claim 11, wherein the plurality of structural members are transparent to radiative electromagnetic energy.

19. The method of claim 11, wherein the housing is configured to house a rechargeable power source configured to power the circuitry, and wherein the time-varying magnetic field is configured to recharge the rechargeable power source.

20. A medical device comprising:
   circuitry configured to at least one of sense a physiological parameter of a patient or deliver a therapy to the patient;
   a rechargeable power source configured to power the circuitry; and
   a housing configured to house the circuitry and the power source, wherein the housing comprises:
      a plurality of ceramic structural members; and
      one or more metallizations brazed onto the plurality of structural members, wherein the one or more metallizations are welded together to join and hermetically seal the plurality of structural members, and wherein the geometry of the metallizations is configured to suppress induced currents in the housing when the medical device is exposed to a time-varying magnetic field to recharge the rechargeable power source.

* * * * *